(12) United States Patent
Moore et al.

(10) Patent No.: US 7,439,352 B2
(45) Date of Patent: *Oct. 21, 2008

(54) PROCESS FOR THE PRODUCTION OF ANHYDROSUGAR ALCOHOLS

(75) Inventors: Kevin M. Moore, Mt. Zion, IL (US); Alexandra J. Sanborn, Lincoln, IL (US); Paul Bloom, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 578 days.

This patent is subject to a terminal disclaimer.

(21) Appl. No.: 10/712,399

(22) Filed: Nov. 14, 2003

(65) Prior Publication Data

US 2004/0152907 A1    Aug. 5, 2004

Related U.S. Application Data

(63) Continuation-in-part of application No. 09/955,672, filed on Sep. 19, 2001, now Pat. No. 6,849,748.

(60) Provisional application No. 60/244,962, filed on Nov. 1, 2000.

(51) Int. Cl.
    *C07H 15/00*      (2006.01)
    *C07H 5/04*      (2006.01)
    *C07H 1/00*      (2006.01)
    *C07H 1/08*      (2006.01)
    *C07D 315/00*      (2006.01)
    *C07D 493/00*      (2006.01)
    *C07C 29/00*      (2006.01)

(52) U.S. Cl. .................. 536/124; 536/18.5; 536/18.6; 536/18.7; 536/55.3; 536/123.1; 536/124; 536/126; 536/127; 549/417; 549/464; 568/902

(58) Field of Classification Search .................. 549/417, 549/464; 536/18.5, 18.6, 18.7, 55.3, 123.1, 536/124, 126, 127; 568/902
See application file for complete search history.

(56) References Cited

U.S. PATENT DOCUMENTS 3,160,641 A    12/1964    Hartmann .................... 529/464

(Continued)

FOREIGN PATENT DOCUMENTS

DE      488 602      12/1929

(Continued)

OTHER PUBLICATIONS

Bahulayan, D., and Sreekumar, K., "Chiral polyesters with azobenzene moieties in the main chain, synthesis and evaluation of nonlinear optical properties," *J. Mater. Chem.* 9:1425-1429, Royal Society of Chemistry (Jul. 1999).

(Continued)

*Primary Examiner*—Taylor Victor Oh
(74) *Attorney, Agent, or Firm*—Craig G. Cochenour; Duane A. Stewart, III; Buchanan Ingersoll & Rooney PC

(57) ABSTRACT

A process is provided for the preparation of anhydrosugar alcohols. The process involves heating a sugar alcohol or a monoanhydrosugar alcohol starting material in the presence of an acid catalyst, and subsequent purification of the anhydrosugar alcohol. In some embodiments of the present invention, film evaporators are used in distillation and purification of the anhydrosugar alcohols. Anhydrosugar alcohols of very high purity are achieved in the practice of the present invention. In some embodiments of the present invention, very high purities of the anhydrosugar alcohols are achieved without the use of organic solvents.

60 Claims, 1 Drawing Sheet

U.S. PATENT DOCUMENTS

Figure 1:
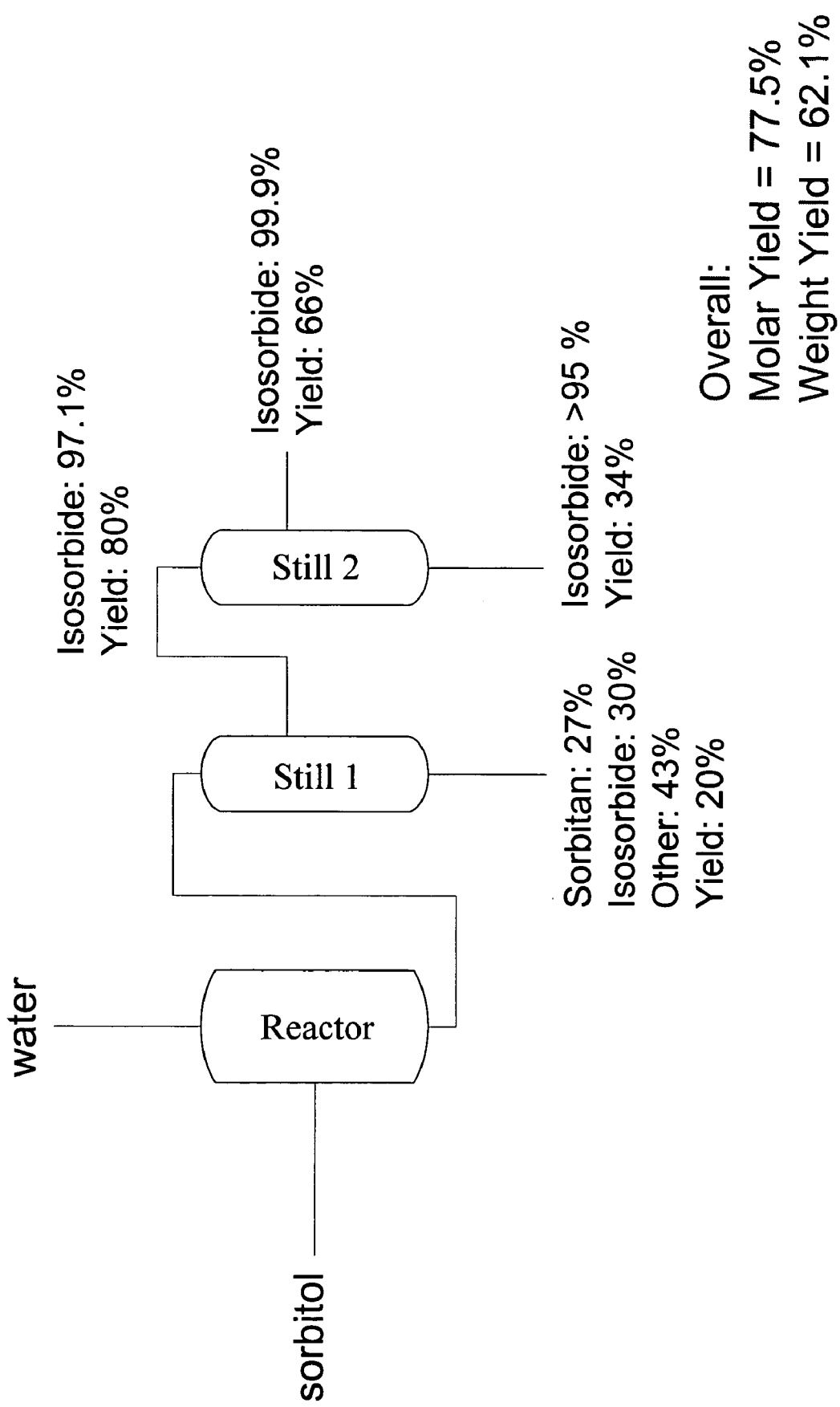

| | | | | |
|---|---|---|---|---|
| 3,454,603 | A | 7/1969 | Hartmann | 549/464 |
| 4,297,290 | A | 10/1981 | Stockburger | 549/678 |
| 4,408,061 | A | 10/1983 | Salzburg et al. | 549/464 |
| 4,506,086 | A | 3/1985 | Salzburg et al. | 549/464 |
| 4,564,692 | A | 1/1986 | Feldmann et al. | 549/464 |
| 4,861,513 | A | 8/1989 | Lueders et al. | 282/182.24 |
| 6,849,748 | B2 * | 2/2005 | Moore et al. | 549/417 |
| 2002/0002291 | A1 | 1/2002 | Bhatia | 549/465 |
| 2002/0052516 | A1 | 5/2002 | Moore et al. | 549/417 |
| 2007/0213544 | A1 * | 9/2007 | Sanborn | 549/417 |

FOREIGN PATENT DOCUMENTS

| | | |
|---|---|---|
| GB | 600 870 | 4/1948 |
| WO | WO 00/14081 | 3/2000 |
| WO | WO 02/36598 A1 | 5/2002 |

OTHER PUBLICATIONS

Bock, K., et al., "Acid Catalyzed Dehydration of Alditols. Part I. $_D$-Glucitol and $_D$-Mannitol," *Acta Chem. Scand.* 35:441-449, Nordic Chemical Societies (1981).

Duclos, A., et al., "A Simple Conversion of Polyols into Anhydroalditols," *Synthesis* 10:1087-1090, Georg Thieme Verlag (1994).

Wiggins, L.F., "Anhydrides of the Penitols and Hexitols," *Adv. Carb. Chem.*, pp. 191-228, Imperial College of Tropical Agriculture (1950).

International Search Report for International Patent Application No. PCT/US01/42880, mailed Apr. 18, 2002.

Fléche, G., and Huchette, M., "Isosorbide. Preparation, Properties and Chemistry," *Starch* 38:26-30, VCH Verlagsgesellschaft mbH (1985).

Goodwin, G., et al., "Preparation of bicyclic hexitol anhydrides by using acidic cation-exchange resin in a binary solvent. 13C-NMR spectroscopy confirms configuration inversion in chloride displacement of methanosulfonate in isomannide and isosorbide derivatives," *Carb. Res.* 79:133-141, Elsevier Scientific Publishing Company (1980).

Koch, H., et al., "New Industrial Products from Starch," *Starch* 40:128-129, Wiley-VCH (1988).

Marr, A., et al., "Synthesis and structure of 1,4:3,6-dianhydro-2-O-p-tosyl-D-mannitol," *J. Chem. Crystal.* 27:161-166, Plenum Publishing Corporation (1997).

Stoss, P., et al., "1,4:3,6-Dianhydrohexitols," *Adv. Carbohydr. Chem. Biochem.* 49:93-173, Academic Press (1991).

Wiggins, L.F., "The Anhydrides of Polyhydric Alcohols. Part I. The Constitution of isoMannide," *J. Chem. Soc.* 4-6, American Chemical Society (1945).

Supplementary European Search Report dated Oct. 2, 2007.

* cited by examiner

US 7,439,352 B2

PROCESS FOR THE PRODUCTION OF ANHYDROSUGAR ALCOHOLS

CROSS-REFERENCE TO RELATED APPLICATIONS

This application is a continuation-in-part of U.S. Utility patent application Ser. No. 09/955,672, filed Sep. 19, 2001, which claims the benefit of U.S. Provisional Patent Application Ser. No. 60/244,962, filed on Nov. 1, 2000. Both applications are hereby incorporated by reference in their entireties.

BACKGROUND OF THE INVENTION

1. Field of the Invention

The present invention relates to the production of anhydrosugar alcohols. More particularly, the present invention relates to a process for the production of anhydrosugar alcohols from sugar alcohol or monoanhydrosugar alcohol starting materials.

2. Related Art

The chemical formation of closed-ring organic molecules has posed many issues for structural organic chemists. This has been particularly true with regard to synthetic reactions involving sugars and polyols, the acid dehydration of which leads to internal anhydro compounds (mono- and dianhydro products). Fleche and Huchette, *Staerke* 38:26-30 (1985) (hereby incorporated by reference in its entirety).

The earliest work in this area was done on 1,4:3,6-dianhydro-D-mannitol by Faucommier in 1884. Only sporadic work followed until the 1940's and 1950's, when intensive work was done on all possible isomers of 1,4:3,6-dianhydrohexitols. Stoss and Hemmer, *Adv. Carbohydrate Chem. and Biochem.* 93-173 (1991) (hereby incorporated by reference in its entirety). Since then a large body of chemical literature has developed in this area.

The 1,5:3,6-dianhydrohexitols belong to the so-called "biomass-derived substances," obtainable from natural products. Therefore, these compounds are classified as "regenerable resources." Furthermore, 1,4:3,6-dianhydrohexitols, such as isosorbide, can be used as starting materials and intermediates in various organic synthetic reaction schemes. For example, isosorbide is useful in the formation of numerous pharmaceutical compounds, in food production, cosmetic production, plastic and polymer production, and in other industrial uses such as in the production of polyurethane, polycarbonate, polyesters, and polyamides. Stoss and Hemmer, 1991. Examples of specific compounds in which isosorbide is used are, isosorbide dimethyl ether, which is useful as an industrial solvent, a pharmaceutical additive, and in personal care products, and isosorbide dinitrate, which is useful as a medication to relieve the pain of angina attacks or reduce the number of such attacks by improving blood flow to the heart.

Of the known isohexides, isosorbide is considered to be that of the highest importance. Stoss and Hemmer (1991) describe the putative steps leading from D-glucitol (also referred to in the art as sorbitol) to isosorbide. Acidic media are generally used for dehydrating the sugar alcohol substrate. Especially to enhance the yield and to avoid side reactions, certain modifications of the reaction conditions have been employed over the years, with various impacts on yield of isosorbide product. Stoss and Hemmer (1991).

Several processes for the production of anhydrosugar alcohols (including isohexides such as isosorbide) are known. For example, PCT application number PCT/US99/00537 (WO 00/14081), discloses collecting methods and a continuous production method with recycling of organic solvent. Most methods involve the use of concentrated acids and organic solvents. Goodwin et al., *Carbohydrate Res.* 79:133-141 (1980) have disclosed a method involving the use of acidic-cation-exchange resin in place of concentrated, corrosive acids, but with low yield of isosorbide product. An alternative is the supersaturation-based method, as disclosed in U.S. Pat. No. 4,564,692 (Feldmann, et al., Jan. 14, 1986). However, a need continues in the art for a process for production of very pure isosorbide, at reasonable yields. The above-cited references are hereby incorporated by reference in their entireties.

BRIEF SUMMARY OF THE INVENTION

The present invention relates to a process for the preparation of anhydrosugar alcohols from sugar alcohol or monoanhydrosugar alcohol starting materials.

In accordance with one aspect of the present invention, there is provided a process for producing an anhydrosugar alcohol comprising heating a pentitol or hexitol sugar alcohol or monanhydrosugar alcohol starting material until molten, dehydrating the starting material in the presence of an acid catalyst to form an anhydrosugar alcohol mixture, and purifying the anhydrosugar alcohol from the anhydrosugar alcohol mixture, wherein the purification comprises distillation in a film evaporator.

In one embodiment, the film evaporator is a wiped film evaporator.

BRIEF DESCRIPTION OF THE DRAWINGS/FIGURES

FIG. 1. A schematic diagram representing one embodiment of the process of the present invention. Sorbitol starting material and water are placed in a reactor with Amberlyst 35 acidic ion exchange resin at a temperature of from about 98° C. to about 120° C. and a pressure of about 10 Torr. The resulting anhydrosugar alcohol mixture is directed to a first film evaporator, where a first anhydrosugar alcohol distillate is formed. The first anhydrosugar alcohol distillate is directed to a second film evaporator to further purify the anhydrosugar alcohol. The isosorbide yields and purities obtained at various stages of the process and locations within the purification apparatus are provided, and are further explained in Example 9.

DETAILED DESCRIPTION OF THE INVENTION

In one embodiment, the invention provides a process for producing an anhydrosugar alcohol comprising: (a) heating a pentitol or hexitol sugar alcohol or monoanhydrosugar alcohol starting material until molten; (b) dehydrating the molten starting material in the presence of an acid catalyst to form an anhydrosugar alcohol mixture; and (c) purifying the anhydrosugar alcohol from the anhydrosugar alcohol mixture, wherein the purification comprises distillation of the anhydrosugar alcohol mixture in a first film evaporator.

In a further embodiment, the first film evaporator is a wiped film evaporator.

In a further embodiment, the acid catalyst a solid acid catalyst.

In a further embodiment, the solid acid catalyst is selected from the group consisting of acidic ion exchange resins and acidic zeolite powders.

In a further embodiment, the solid acid catalyst is an acidic ion exchange resin. In another embodiment, the acidic ion exchange resin is selected from the group consisting of AG50W-X12, Amberlyst 35, Amberlyst 15, RCP21H, and Dowex 50W×4. In another embodiment, the acidic ion exchange resin is Amberlyst 35.

In a further embodiment, the acidic ion exchange resin is present in an amount of from about 0.01 gram equivalents to about 0.15 gram equivalents of resin to sugar alcohol or monoanhydrosugar alcohol starting material.

In a further embodiment, the solid acid catalyst is an acidic zeolite powder. In one embodiment, the acidic zeolite powder is selected from the group consisting of CBV 3024, 5534G, T-2665, and T-4480.

In a further embodiment, the acid catalyst is a soluble acid catalyst. In one embodiment, the soluble acid catalyst is selected from the group consisting of sulfuric acid, phosphoric acid, p-toluenesulfonic acid, and p-methanesulfonic acid.

In a further embodiment, the purification further comprises recrystallization of the anhydrosugar alcohol. In another embodiment, the recrystallization is a melt recrystallization. In another embodiment, the recrystallization is a solvent recrystallization. In one embodiment, the solvent recrystallization comprises heating said anhydrosugar alcohol with a solvent followed by gradual cooling at a rate of from about 8° C. to about 12° C. per minute. In one embodiment, the solvent recrystallization is performed with acetone.

In a further embodiment, the purification further comprises a solvent wash followed by filtration. In another embodiment, the solvent wash is performed with a solvent which, for example, comprises methanol, acetone, ethyl acetate, and/or ethanol. In another embodiment, the solvent wash is performed with acetone.

In a further embodiment, the purification further comprises distillation of the anhydrosugar alcohol mixture in a second film evaporator. In another embodiment, the second film evaporator is a wiped film evaporator. In another embodiment, the distillation in the second film evaporator is performed under the same temperature and pressure conditions as the distillation in the first film evaporator.

In a further embodiment, the process further comprises separation of the anhydrosugar alcohol by centrifugation. In another embodiment, the process further comprises separation of the anhydrosugar alcohol by filtration.

In a further embodiment, the sugar alcohol or monoanhydrosugar alcohol starting material is selected from the group consisting of arabinitol, ribitol, sorbitol, mannitol, galactitol, iditol, and mixtures thereof. In another embodiment, the sugar alcohol or monoanhydrosugar alcohol starting material is sorbitol. In another embodiment, the sugar alcohol or monoanhydrosugar alcohol starting material is mannitol.

In a further embodiment, the anhydrosugar alcohol is a dianhydrohexitol. In one embodiment, the dianhydrohexitol is isosorbide. In another embodiment, the anhydrosugar alcohol is isomannide.

In a further embodiment, dehydration is performed at a temperature of from about 98° C. to about 191° C. In another embodiment, the dehydration is performed at a temperature of from about 98° C. to about 130° C. In another embodiment, the dehydration is performed at a temperature of from about 98° C. to about 120° C. In another embodiment, the dehydration is performed at a temperature of from about 120° C. to about 130° C. In another embodiment, the dehydration is performed at a temperature of from about 125° C. to about 130° C.

In a further embodiment, the dehydration is performed at a vacuum pressure of from about 0.01 Torr to about 40 Torr. In another embodiment, the dehydration is performed at a vacuum pressure of from about 0.01 Torr to about 10 Torr. In another embodiment, the dehydration is performed at a vacuum pressure of from about 1 Torr to about 10 Torr.

In a further embodiment, the distillation in the first film evaporator is performed at a vapor temperature of from about 120° C. to about 190° C. and a pot temperature of at least the distilling point of the dehydrated anhydrosugar alcohol. In another embodiment, the distillation in the first film evaporator is performed at a vapor temperature of from about 160° C. to about 180° C. and a pot temperature of at least the distilling point of the dehydrated anhydrosugar alcohol. In another embodiment, the distillation in the first film evaporator is performed at a vapor temperature of from about 165° C. to about 170° C. and a pot temperature of at least the distilling point of the dehydrated anhydrosugar alcohol. In another embodiment, the distillation in the the film evaporator is performed at a vapor temperature of about 170° C. and a pot temperature of at least the distilling point of the dehydrated anhydrosugar alcohol.

In a further embodiment, the distillation in the first film evaporator is performed at a vacuum pressure of from about 0.01 Torr to about 40 Torr. In another embodiment, the distillation in the first film evaporator is performed at a vacuum pressure of from about 0.1 Torr to about 10 Torr. In another embodiment, the distillation in the first film evaporator is performed at a vacuum pressure of from about 1 Torr to about 10 Torr.

In one embodiment, the invention provides a process for producing an anhydrosugar alcohol comprising: (a) heating a pentitol or hexitol sugar alcohol or monoanhydrosugar alcohol starting material until molten; (b) dehydrating the molten starting material in the presence of a solid acid catalyst to form an anhydrosugar alcohol mixture; (c) distilling the anhydrosugar alcohol mixture in a first film evaporator to produce a first anhydrosugar alcohol distillate; and (d) further purifying the anhydrosugar alcohol from the first anhydrosugar alcohol distillate.

In a further embodiment, the first film evaporator is a wiped film evaporator.

In a further embodiment, the further purification of the first anhydrosugar distillate comprises distillation of the first anhydrosugar alcohol distillate in a second film evaporator. In a further embodiment, the second film evaporator is a wiped film evaporator.

In a further embodiment, the further purification of the first anhydrosugar distillate comprises solvent recrystallization of the first anhydrosugar alcohol distillate. In another embodiment, the further purification of the first anhydrosugar distillate comprises melt recrystallization of the first anhydrosugar alcohol distillate. In another embodiment, the further purification of the first anhydrosugar distillate comprises a solvent wash followed by a filtration.

In a further embodiment, the dehydration is performed at a temperature of from about 120° C. to about 130° C.

In a further embodiment, the dehydration is performed at a vacuum pressure of from about 1 Torr to about 10 Torr.

In a further embodiment, the distillation in the first film evaporator is performed at a vapor temperature of from about 165° C. to about 170° C. and a pot temperature of at least the distilling point of the dehydrated anhydrosugar alcohol.

In a further embodiment, the distillation in the first film evaporator is performed at a vacuum pressure of from about 1 Torr to about 10 Torr.

In a further embodiment, the sugar alcohol or monoanhydrosugar alcohol starting material is sorbitol.

In a further embodiment, the anhydrosugar alcohol is isosorbide.

In a further embodiment, the solid acid catalyst is an acidic ion exchange resin. In another embodiment, the acidic ion exchange resin is Amberlyst 35. In a another embodiment, the solid acid catalyst is a zeolite powder.

In one embodiment, the invention provides a process for producing isosorbide comprising: (a) heating sorbitol powder at a temperature of from about 98° C. to about 105° C. until molten; (b) dehydrating the melted sorbitol in the presence of an acidic ion exchange resin, under vacuum pressure of from about 1 Torr to about 10 Torr, and at a temperature of from about 120° C. to about 130° C. to form an isosorbide mixture, wherein the acidic ion exchange is resin present in an amount of from about 0.01 gram equivalents to about 0.15 gram equivalents of resin to sugar alcohol or monoanhydrosugar alcohol starting material; (c) subjecting the isosorbide mixture to a first distillation at a pot temperature of from about 160° C. to about 170° C., a vapor temperature of from about 160° C. to about 190° C., and a vacuum pressure of from about 1 Torr to about 10 Torr to form a first isosorbide distillate, wherein the first distillation is performed in a wiped film evaporator; (d) subjecting the first isosorbide distillate to a second distillation at a pot temperature of from about 160° C. to about 170° C., a vapor temperature of from about 160° C. to about 190° C., and a vacuum pressure of from about 1 Torr to about 10 Torr to form a purified isosorbide, wherein the second distillation is performed in a wiped film evaporator; and (e) collecting the purified isosorbide.

In another embodiment, the invention provides a process for producing isomannide comprising: (a) heating mannitol at a temperature of from about 98° C. to about 105° C. until molten; (b) dehydrating the melted mannitol in the presence of an acidic ion exchange resin, under vacuum pressure of from about 1 Torr to about 10 Torr, and at a temperature of from about 120° C. to about 130° C. to form an isomannide mixture, wherein the acidic ion exchange is resin present in an amount of from about 0.01 gram equivalents to about 0.15 gram equivalents of resin to sugar alcohol or monoanhydrosugar alcohol starting material; (c) subjecting the isomannide mixture to a first distillation at a pot temperature of from about 160° C. to about 170° C., a vapor temperature of from about 160° C. to about 190° C., and a vacuum pressure of from about 1 Torr to about 10 Torr to form a first isomannide distillate, wherein the first distillation is performed in a wiped film evaporator; (d) subjecting the first isomannide distillate to a second distillation at a pot temperature of from about 160° C. to about 170° C., a vapor temperature of from about 160° C. to about 190° C., and a vacuum pressure of from about 1 Torr to about 10 Torr to form a purified isomannide, wherein the second distillation is performed in a wiped film evaporator; and (e) collecting the purified isomannide.

Starting Materials

Typical sugar alcohols, particularly pentitols and hexitols, are suitable for use as starting materials in the process of the invention. As used herein, "pentitol" refers to a sugar alcohol or monoanhydrosugar alcohol having five carbon atoms (e.g., ribitol). As used herein, "hexitol" refers to a sugar alcohol or monoanhydrosugar alcohol having six carbon atoms (e.g., sorbitol or mannitol). The starting materials can include sugar alcohols or monoanhydrosugar alcohols, or a mixture of such sugar alcohols or monoanhydrosugar alcohols. Examples of starting materials include, but are not limited to, arabinitol, ribitol, D-glucitol (also referred to in the art as D-sorbitol or sorbitol, and referred to herein as sorbitol), D-mannitol (or mannitol), galactitol (dulcitol), iditol, and the like. Sorbitol is a particularly preferred starting material because it is readily available, and because pure isosorbide is very useful in a number of chemical and pharmaceutical applications.

In the first step of the process of the present invention, the selected starting material is melted by standard methods that are known in the art. For example, the starting material can be melted by placing it in a 3-neck round bottom flask equipped with an agitator, temperature probe, and vacuum line. If, by way of example, sorbitol is the starting material, it is heated to at least about 100° C. to about 200° C. For sorbitol powder, to provide a specific example, the preferred melting temperature is from about 98° C. to about 105° C.; an even more preferred melting temperature is from about 98° C. to about 100° C. Once molten, the sorbitol is subject to stirring. One of skill in the art would be familiar with the specific melting points of other sugar alcohols and monoanhydrosugar alcohols. Generally, they fall between about 60° C. and about 200° C.

Catalysts and Dehydration

A catalyst that will facilitate the dehydration of the sugar alcohol is then added to the molten starting material. Typically the catalysts used to facilitate the dehydration of sugar alcohols are acid catalysts. The classes of acid catalysts useful in the practice of the present invention include, but are not limited to, soluble acids, acidic ion exchange resins, and inorganic ion exchange materials.

Soluble acids. In some embodiments, the acid catalyst of the present invention comprises a soluble acid. Soluble acids including, but not limited to, sulfuric acid, phosphoric acid, p-toluenesulfonic acid, and p-methanesulfonic acid are preferred for use in the present invention. One of skill in the art would recognize that other soluble acids with similar properties may be useful in the present invention although not specifically listed here.

Zeolites. Zeolite powders are inorganic ion exchange materials. In some embodiments, the acid catalyst of the present invention comprises a zeolite powder, specifically an acidic zeolite powder, and more specifically, a type ZSM-5 ammonium form zeolite powder. Examples of zeolite powders that are useful in the practice of the present invention include, but are not limited to, CBV 3024 or CBV 5534G (both available from Zeolyst International), and/or T-2665 or T-4480 (both available from United Catalysis, Inc.). One of skill in the art would recognize that other zeolite powders with similar properties may be useful in the present invention although not specifically listed here.

Acidic Ion Exchange Resins. In some embodiments, the acid catalyst of the present invention comprises an acidic ion exchange resin, specifically a sulfonated divinylbenzene/styrene co-polymer acidic ion exchange resin. Examples of acidic ion exchange resins useful in the practice of the present invention include, but are not limited to, AG50W-X12 from BioRad Laboratories, Amberlyst 15 or Amberlyst 35 from Rohm & Haas, RCP21H from Mitsubishi Chemical Corp., and Dowex 50W×5 (Dow Chemical Co.). The sulfonated divinylbenzene/styrene co-polymer acidic ion exchange resin, Amberlyst 35, is a particularly preferred resin in the practice of the present invention, specifically for the production of isosorbide from sorbitol. One of skill in the art would recognize that other acidic ion exchange resins with similar properties may be useful in the present invention although not specifically listed here.

The amount of catalyst used will vary depending upon the reaction conditions and starting material, as those of skill in the art will appreciate, but will generally be on the order of from about 0.01 equivalents to about 0.15 equivalents by weight. A preferred amount of catalyst is about 0.1 equivalents by weight.

It is possible to perform one or more dehydrations of the starting sugar alcohol during the reaction, producing, for example, a mono- or dianhydrosugar alcohol. The reaction may also be controlled so as to produce a combination of mono- and dianhydrosugar alcohols by adjusting either the reaction conditions or the starting materials, which as those of skill in the art will appreciate, could contain both sugar alcohols and monoanhydrosugar alcohols.

The dehydration in the presence of the catalyst can be carried out under a vacuum, at elevated temperatures, and with stirring of the reaction mixture. The vacuum can range over a pressure of from about 0.05 Torr to about 40 Torr, with preferred pressures of from about 1 Torr to about 10 Torr. As a specific example, a preferred pressure for the dehydration step in the process of the present invention in which isosorbide is made from sorbitol is from about 1 Torr to a bout 10 Torr. The temperature for the dehydration can be from about 90° C. to about 140° C. Specifically, the dehydration temperature can be from about 98° C. to about 130° C., and more specifically, the dehydration temperature can be from about 120° C. to about 130° C. In the production of isosorbide from sorbitol, for example, the dehydration can be carried out for approximately 2 hours, with constant stirring, at a temperature of about 120° C. The water can be pulled off of the melted sorbitol/catalyst mixture under a vacuum of from about 1 Torr to about 10 Torr. The dehydration reaction is preferably performed in a reactor which can run in a batch or continuous mode. In embodiments wherein the acid catalyst is a solid acid catalyst (e.g., acidic ion exchange resin), the reactor can preferably hold or contain baskets to which the solid acid catalyst can be added.

It will, of course, be appreciated by those of skill in the art that, in a process such as that of the present invention that involves application of both elevated temperatures and vacuum, the specific parameters of the process, including the time it takes to carry certain steps to completion, will vary depending upon the temperatures and pressures used. For example, the inventors have determined that higher vacuum levels for the distillation step gave the expected lower distillation temperature. An additional variable is the selected starting material, which will have a particular melting and/or distillation point (the latter being dependent upon the vacuum). This is equally true for the purification processes described below. However, given the disclosure presented herein, it is within the level of skill in the art to optimize the process parameters of the invention for a particular application. This can be done with only a few preliminary experiments, and without undue experimentation, in light of the instant disclosure.

Purification

Following the dehydration procedure, the resultant anhydrosugar alcohol mixture is purified. In one embodiment, a vacuum distillation is used. In a more specific embodiment, the vacuum distillation is performed using a film evaporator, specifically a wiped film evaporator. One example of a wiped film evaporator apparatus that is useful in the present invention is a vertical agitated thin-film processor. Advantages of using a wiped film evaporator include handling of viscous solutions, improved product purity, and low residence time, which leads to a reduction or elimination of product degradation. Specifically with respect to production of isosorbide from sorbitol, use of a wiped film evaporator provides approximately 80% yield on distillation, negligible water loss during distillation (which results in reduced polymerization), and provides for further recovery of isosorbide and sorbitan from the residue. The distillation process results in a first anhydrosugar alcohol distillate.

As noted above, the parameters for vacuum distillation will vary depending upon the material to be purified, and the temperature and pressure, as will be appreciated by those of ordinary skill in the art. The pot temperature will depend upon the temperature at which the material to be purified distills (i.e., the distillation point), which, again, will depend on the vacuum applied in the system. For example, in the case of isosorbide, a range of vapor temperatures of from about 140° C. to about 190° C. is preferred; more preferred is from about 160° C. to about 170° C.; even more preferred is from about 165° C. to about 170° C. The vacuum pressure can be from about 0.05 Torr to about 40 Torr; preferably from about 1 Torr to about 10 Torr. For example, and specifically with regard to vacuum distillation of isosorbide, a vacuum pressure of from about 1 Torr to about 10 Torr, a pot temperature of about 180° C., and a vapor temperature of from about 160° C. to about 170° C. are most preferred.

Alternative purification methods of the anhydrosugar alcohol mixture such as filtration of the anhydrosugar alcohol mixture, or the addition of activated charcoal with subsequent crystallization of the anhydrosugar alcohol mixture, are also useful in the present invention.

In one embodiment, in order to further purify and isolate the anhydrosugar alcohol, the first anhydrosugar alcohol distillate is subjected to a second vacuum distillation, specifically in a film evaporator, and more specifically in a wiped film evaporator. The second wiped film evaporator can be of the same type as, or different than, the first wiped film evaporator. The conditions (e.g., vacuum pressure and temperature) of the second vacuum distillation can be the same as, or different than, the conditions of the first vacuum distillation, the parameters of which are described above. The use of two film evaporators allows for production and purification of anhydrosugar alcohols, specifically isosorbide, without the use of potentially harmful organic solvents.

In another embodiment, in order to further purify and isolate the anhydrosugar alcohol, the first anhydrosugar alcohol distillate is subjected to melt crystallization. The recovered distillate product is heated to its melting point (e.g., for isosorbide, to approximately 65° C.) until molten, and then cooled over time until the crystallization point is reached, but not so much that the material solidifies. In fact, a slurry-like consistency is preferred, so that the material can be centrifuged. As used herein, the term "slurry-like consistency" refers to recrystallized anhydrosugar alcohol distillate that is a mixture of liquid with several finely divided particles. The centrifugation is performed at a relatively high speed for a relatively short period of time in order to avoid solidification of the material, and also to avoid having the desired purified anhydrosugar alcohol end product be drawn off with the remaining impurities. For example, the centrifugation can be performed at about 3000 to about 4000 rpm for about 5 minutes. However, one of skill in the art will appreciate that the time of the centrifugation will vary depending on the amount of material to be purified. The resultant anhydrosugar alcohol product can be at least 98% pure, and in most cases will be greater than 99% pure (depending upon the solidity of the "slurry"). Alternatively, the first anhydrosugar alcohol distillate is subjected to solvent recrystallization in order to further purify and isolate the anhydrosugar alcohol. Solvents that are useful in the present invention include, but are not limited to, acetone, ethyl acetate, and low molecular weight alcohols such as ethanol and methanol.

In another embodiment, in order to further purify and isolate the anhydrosugar alcohol, the first anhydrosugar alcohol distillate can subjected to a solvent wash followed by filtration. Preferably, the solvents are cold, specifically at a temperature of about 0° C. to about 23° C. Solvents that are useful in the present invention include, but are not limited to, acetone, ethyl acetate, and low molecular weight alcohols such as ethanol and methanol. Filtration can be carried out be means that are well known in the art.

The present invention is described in further detail in the following non-limiting examples.

EXAMPLES

Example 1

This Example describes the production of very high purity isosorbide from sorbitol using a particularly preferred embodiment of the process of the present invention.

Sorbitol powder (180.6 grams, 0.99 mol) was placed in a 3-neck round bottom flask equipped with an agitator, temperature probe, and vacuum line. The sorbitol was heated to approximately 100° C. until molten. An acidic ion exchange resin, Amberlyst 35 (Rohm & Haas) (19.8 grams), was added and vacuum was applied at from about 1 Torr to about 10 Torr. The temperature was increased to from about 120° C. to about 130° C. These temperatures and vacuum parameters were maintained for approximately 2 hours, with constant stirring. The resultant mixture was then vacuum distilled at from about 1 Torr to about 10 Torr, pot temperature of 180° C., and vapor temperature of 170° C. The distillate was collected and subjected to melt crystallization by heating to approximately 65° C. until molten, then cooling, over about 30 minutes to about 45 minutes to approximately 35° C., at which temperature a slurry-like solution was formed. This solution was then quickly centrifuged (in order to avoid solidification), and the resultant isosorbide product had a purity of 99.3%, with an overall yield of 48%.

Example 2

The same apparatus and the same operational conditions—except those specified below—as in Example 1 were used. Upon heating sorbitol to about 100° C. to a molten state, an acidic ion exchange resin, Amberlyst 15 (Rohm and Haas, 24.2 g), was added and vacuumed applied (5-7 Torr). Heating was increased to 135° C., and the reaction allowed to stir continuously for about 2 hours. The resulting mixture contained 64.5% isosorbide and was then purified by the procedure described in Example 1.

Example 3

The same apparatus and the same operational conditions—except those specified below—as in Example 1 were used. Upon heating sorbitol to about 100° C. to a molten state, an acidic ion exchange resin, Dowex 50WX4, (18.1 g), was added and vacuumed applied (7-9 Torr). Heating was increased to 135° C., and the reaction allowed to stir continuously for about 2 hours. The reaction mixture contained 64.1% isosorbide. Purification was then performed.

Example 4

The same apparatus and the same operational conditions—except those specified below—as in Example 1 were used. Upon heating sorbitol to about 100° C. to a molten state, the acidic ion exchange resin, Amberlyst 35 (Rohm and Haas, 11.7 g), was added and vacuumed applied (9-12 Torr). Heating was increased to 135° C., and the reaction allowed to stir continuously for about 2 hours. The resulting mixture contained 18.6% sorbitan and 73.4% isosorbide. The mixture was then purified using the above described procedure.

Example 5

The same apparatus and the same operational conditions—except those specified below—as in Example 1 were used. Upon heating sorbitol to about 100° C. to a molten state, the acidic ion exchange resin, RCP21H (Mitsubishi Chemical Corporation, 12.9 g), was added and vacuumed applied (7-9 Torr). Heating was increased to 135° C., and the reaction allowed to stir continuously under vacuum for about 5 hours. The resulting mixture contained 68.9% isosorbide. The mixture was then purified using the above described procedure.

Example 6

The same apparatus and the same operational conditions—except those specified below—as in Example 1 were used. Sorbitol (221.4 g, 0.99 mol) was heated to about 100° C. to a molten state. At this time, a sulfated zirconia pellet (#416/03 Japan Energy Corporation, 57.7 g), was added and vacuumed applied (5-7 Torr). Heating was increased to 150° C., and the reaction allowed to stir continuously for about 7 hours. The resulting mixture contained 2.2% sorbitol, 56.0% sorbitan and 22.9% isosorbide.

Example 7

Mannitol powder (1082 grams) was placed in a 3-neck round bottom flask equipped with an agitator, temperature probe, and vacuum line. The mannitol was heated to approximately 100° C. until molten. An acidic ion exchange resin, Amberlyst 35 (Rohm & Haas) (60.1 grams), was slowly added and vacuum was applied at from about 1 Torr to about 10 Torr. The temperature was increased to from about 130° C. to about 140° C. These temperature and vacuum parameters were maintained for approximately 2 hours, with constant stirring. The resultant mixture was then vacuum distilled at about 1 Torr to about 10 Torr, pot temperature of 180° C., and vapor temperature of 170° C. The distillate was collected and subjected to recrystallization using acetone to provide a product having an isomannide purity of about 97%.

Example 8

Isosorbide that was distilled in a wiped film evaporator was at about 97% purity. About 1143.0 g of the isosorbide was recrystallized with about 395.0 g of acetone. The temperature was reduced from about 56° C. to about 25° C. at approximately 10° C. per minute The yield of recrystallized dried isosorbide was about 90% (or about 999.8 g), and the purity was about 99.6%. Additional isosorbide was also recovered from the mother liquor.

Example 9

In accordance with the schematic diagram of FIG. 1, sorbitol was added to reactor 1, where it was heated until molten, and the catalyst was added. Sorbitol dehydration was performed and the water was removed under vacuum during the reaction. The product material was transferred to a first still, specifically, a film evaporator, where the first distillation occurred. The resulting pot materials were sorbitan, isosorbide, and other materials. The first distillate was carried to a second still, specifically, a second film evaporator, where the second distillation occurred. The end products were a yield of about 80% isosorbide having about 97.1% purity, and a yield of about 66% isosorbide having about 99.9% purity.

Having now fully described the present invention in some detail by way of illustration and example for purposes of clarity of understanding, it will be obvious to one of ordinary skill in the art that the invention can be performed by modifying or changing the invention with a wide and equivalent range of conditions, formulations and other parameters thereof. Furthermore, it will be obvious to the skilled practitioner that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A process for producing an anhydrosugar alcohol comprising: (a) heating a pentitol or hexitol sugar alcohol or monoanhydrosugar alcohol starting material until molten; (b) dehydrating said molten starting material in the presence of a solid acid catalyst selected from at least one member of the group consisting of an acidic ion exchange resin and an acidic zeolite powder and without a solvent to form an anhydrosugar alcohol mixture; and (c) purifying said anhydrosugar alcohol from said anhydrosugar alcohol mixture, wherein said purification comprises distillation of said anhydrosugar alcohol mixture in a first film evaporator.

2. The process of claim 1, wherein said first film evaporator is a wiped film evaporator.

3. The process of claim 1, wherein said solid acid catalyst is an acidic ion exchange resin.

4. The process of claim 3, wherein said acidic ion exchange resin is selected from the group consisting of AG50W-X 12, Amberlyst 35, Amberlyst 15, RCP21H, and Dowex 50Wx4.

5. The process of claim 4, wherein said acidic ion exchange resin is Amberlyst 35.

6. The process of claim 3, wherein said acidic ion exchange resin is present in an amount of from about 0.01 gram equivalents to about 0.15 gram equivalents of resin to sugar alcohol or monoanhydrosugar alcohol starting material.

7. The process of claim 1, wherein said solid acid catalyst is an acidic zeolite powder.

8. The process of claim 7, wherein said acidic zeolite powder is selected from the group consisting of CBV 3024, 5534G, T-2665, and T-4480.

9. The process of claim 1, wherein said purification further comprises recrystallization of said anhydrosugar alcohol.

10. The process of claim 9, wherein said recrystallization is a melt recrystallization.

11. The process of claim 9, wherein said recrystallization is a solvent recrystallization.

12. The process of claim 11, wherein the solvent is acetone.

13. The process of claim 11, wherein said solvent recrystallization comprises heating said anhydrosugar alcohol with a solvent followed by gradual cooling at a rate of from about 8° C. to 12° C. per minute.

14. The process of claim 1, wherein said purification further comprises a solvent wash followed by a filtration.

15. The process of claim 14, wherein said solvent is selected from the group consisting of acetone, ethyl acetate, and ethanol.

16. The process of claim 15, wherein said solvent is acetone.

17. The process of claim 16, wherein said acetone is at a temperature of from about 0° C. to about 23° C.

18. The process of claim 1, wherein said purification further comprises distillation of said anhydrosugar alcohol mixture in a second film evaporator.

19. The process of claim 18, wherein said second film evaporator is a wiped film evaporator.

20. The process of claim 18, wherein said distillation in said second film evaporator is performed under the same temperature and pressure conditions as the distillation in said first film evaporator.

21. The process of claim 1, further comprising separation of said anhydrosugar alcohol by centrifugation.

22. The process of claim 1, further comprising separation of said anhydrosugar alcohol by filtration.

23. The process of claim 1, wherein said sugar alcohol or monoanhydrosugar alcohol starting material is selected from the group consisting of arabinitol, ribitol, sorbitol, mannitol, galactitol, iditol, and mixtures thereof.

24. The process of claim 23, wherein said sugar alcohol or monoanhydrosugar alcohol starting material is sorbitol.

25. The process of claim 23, wherein said sugar alcohol or monoanhydrosugar alcohol starting material is mannitol.

26. The process of claim 1, wherein said anhydrosugar alcohol is a dianhydrohexitol.

27. The process of claim 26, wherein said dianhydrohexitol is isosorbide.

28. The process of claim 1, wherein said dehydration is performed at a temperature of from 98° C. to about 191° C.

29. The process of claim 1, wherein said dehydration is performed at a temperature of from about 98° C. to about 130° C.

30. The process of claim 1, wherein said dehydration is performed at a temperature of from about 98° C. to about 120° C.

31. The process of claim 1, wherein said dehydration is performed at a temperature of from about 120° C. to about 130° C.

32. The process of claim 1, wherein said dehydration is performed at a temperature of from about 125° C. to about 130° C.

33. The process of claim 1, wherein said dehydration is performed at a vacuum pressure of from about 0.01 Torr to about 40 Torr.

34. The process of claim 1, wherein said dehydration is performed at a vacuum pressure of from about 0.01 Torr to about 10 Torr.

35. The process of claim 1, wherein said dehydration is performed at a vacuum pressure of from about 1 Torr to about 10 Torr.

36. The process of claim 1, wherein said distillation in said first film evaporator is performed at a vapor temperature of from about 120° C. to about 190° C. and a pot temperature of at least the distilling point of the dehydrated anhydrosugar alcohol.

37. The process of claim 1, wherein said distillation in said first film evaporator is performed at a vapor temperature of from about 160° C. to about 180° C. and a pot temperature of at least the distilling point of the dehydrated anhydrosugar alcohol.

38. The process of claim 1, wherein said distillation in said first film evaporator is performed at a vapor temperature of from about 165° C. to about 170° C. and a pot temperature of at least the distilling point of the dehydrated anhydrosugar alcohol.

39. The process of claim 1, wherein said distillation in said first film evaporator is performed at a vapor temperature of about 170° C. and a pot temperature of at least the distilling point of the dehydrated anhydrosugar alcohol.

40. The process of claim 1, wherein said distillation in said first film evaporator is performed at a vacuum pressure of from about 0.01 Torr to about 40 Torr.

41. The process of claim 1, wherein said distillation in said first film evaporator is performed at a vacuum pressure of from about 0.1 Torr to about 10 Torr.

42. The process of claim 1, wherein said distillation in said first film evaporator is performed at a vacuum pressure of from about 1 Torr to about 10 Torr.

43. A process for producing an anhydrosugar alcohol comprising: (a) heating a pentitol or hexitol sugar alcohol or monoanhydrosugar alcohol starting material until molten; (b) dehydrating said molten starting material in the presence of a solid acid catalyst and without a solvent to form an anhydrosugar alcohol mixture, wherein said solid acid catalyst is at least one member of the group consisting of an acidic ion exchange resin and an acidic zeolite powder; (c) distilling said anhydrosugar alcohol mixture in a first film evaporator to produce a first anhydrosugar alcohol distillate; and (d) further purifying said anhydrosugar alcohol from said first anhydrosugar alcohol distillate.

44. The process of claim 43, wherein said first film evaporator is a wiped film evaporator.

45. The process of claim 43, wherein said further purification of said first anhydrosugar alcohol distillate comprises distillation of said first anhydrosugar alcohol distillate in a second film evaporator.

46. The process of claim 45, wherein said second film evaporator is a wiped film evaporator.

47. The process of claim 43, wherein said further purification of said first anhydrosugar alcohol distillate comprises solvent recrystallization of said first anhydrosugar alcohol distillate.

48. The process of claim 43, wherein said further purification of said first anhydrosugar alcohol distillate comprises melt recrystallization of said first anhydrosugar alcohol distillate.

49. The process of claim 43, wherein said further purification of said first anhydrosugar alcohol distillate comprises a solvent wash followed by a filtration.

50. The process of claim 43, wherein said dehydration is performed at a temperature of from about 120° C. to about 130° C.

51. The process of claim 43, wherein said dehydration is performed at a vacuum pressure of from about 1 Torr to about 10 Torr.

52. The process of claim 43, wherein said distillation in said first film evaporator is performed at a vapor temperature of from about 165° C. to about 170° C. and a pot temperature of at least the distilling point of the dehydrated anhydrosugar alcohol.

53. The process of claim 43, wherein said distillation in said first film evaporator is performed at a vacuum pressure of from about 1 Torr to about 10 Torr.

54. The process of claim 43, wherein said sugar alcohol or monoanhydrosugar alcohol starting material is sorbitol.

55. The process of claim 43, wherein said anhydrosugar alcohol is isosorbide.

56. The process of claim 43, wherein said sugar alcohol or monoanhydrosugar alcohol starting material is mannitol.

57. The process of claim 43, wherein said anhydrosugar alcohol is isomannide.

58. The process of claim 43, wherein said acidic ion exchange resin is Amberlyst 35.

59. A process for producing isosorbide comprising: (a) heating sorbitol powder at a temperature of from about 98° C. to about 105° C. until molten; (b) dehydrating said melted sorbitol in the presence of an acidic ion exchange resin, without a solvent, under vacuum pressure of from about 1 Torr to about 10 Torr, and at a temperature of from about 120° C. to about 130° C. to form an isosorbide mixture, wherein said acidic ion exchange is resin present in an amount of from about 0.01 gram equivalents to about 0.15 gram equivalents of resin to sugar alcohol or monoanhydrosugar alcohol starting material; (c) subjecting said isosorbide mixture to a first distillation at a pot temperature of from about 160° C. to about 170° C., a vapor temperature of from about 160° C. to about 190° C., and a vacuum pressure of from about 1 Torr to about 10 Torr to form a first isosorbide distillate, wherein said first distillation is performed in a wiped film evaporator; (d) subjecting said first isosorbide distillate to a second distillation at a pot temperature of from about 160° C. to about 170° C., a vapor temperature of from about 160° C. to about 190° C., and a vacuum pressure of from about 1 Torr to about 10 Torr to form a purified isosorbide, wherein said second distillation is performed in a wiped film evaporator; and (e) collecting said purified isosorbide.

60. A process for producing isomannide comprising: (a) heating mannitol at a temperature of from about 98° C. to about 105° C. until molten; (b) dehydrating said melted mannitol in the presence of an acidic ion exchange resin, without a solvent, under vacuum pressure of from about 1 Torr to about 10 Torr, and at a temperature of from about 120° C to about 130° C. to form an isomannide mixture, wherein said acidic ion exchange is resin present in an amount of from about 0.01 gram equivalents to about 0.15 gram equivalents of resin to sugar alcohol or monoanhydrosugar alcohol starting material; (c) subjecting said isomannide mixture to a first distillation at a pot temperature of from about 160° C. to about 170° C., a vapor temperature of from about 160° C. to about 190° C., and a vacuum pressure of from about 1 Torr to about 10 Torr to form a first isomannide distillate, wherein said first distillation is performed in a wiped film evaporator; (d) subjecting said first isomannide distillate to a second distillation at a pot temperature of from about 160° C. to about 170° C. a vapor temperature of from about 160° C. to about 190° C., and a vacuum pressure of from about 1 Torr to about 10 Torr to form a purified isomannide, wherein said second distillation is performed in a wiped film evaporator; and (e) collecting said purified isomannide.

* * * * *